US012791487B2

(12) United States Patent
Kangas et al.

(10) Patent No.: US 12,791,487 B2
(45) Date of Patent: Nov. 10, 2026

(54) METHOD AND SYSTEM FOR ANALYZING THE ELEMENTAL CONTENT OF DRILL CORES

(71) Applicant: Lumo Analytics OY, Helsinki (FI)

(72) Inventors: Lasse Kangas, Helsinki (FI); Ari Hartikainen, Espoo (FI); Jaakko Roima, Helsinki (FI)

( * ) Notice: Subject to any disclaimer, the term of this patent is extended or adjusted under 35 U.S.C. 154(b) by 178 days.

(21) Appl. No.: 18/861,656

(22) PCT Filed: Apr. 28, 2023

(86) PCT No.: PCT/FI2023/000002
§ 371 (c)(1),
(2) Date: Oct. 30, 2024

(87) PCT Pub. No.: WO2023/209270
PCT Pub. Date: Nov. 2, 2023

(65) Prior Publication Data
US 2026/0251577 A1 Aug. 27, 2026

(30) Foreign Application Priority Data
Apr. 30, 2022 (FI) ..................................... 20227064
Jul. 6, 2022 (FI) ..................................... 20227096

(51) Int. Cl.
*G01N 21/71* (2006.01)
*E21B 25/00* (2006.01)
(Continued)

(52) U.S. Cl.
CPC ......... *G01N 21/718* (2013.01); *E21B 25/005* (2013.01); *E21B 49/00* (2013.01);
(Continued)

(58) Field of Classification Search
CPC .......... E21B 49/00; E21B 49/02; E21B 25/00; E21B 25/005; E21B 25/16; G01B 11/30;
(Continued)

(56) References Cited

U.S. PATENT DOCUMENTS 11,105,785 B2 * 8/2021 Artursson ................ G01N 1/08
12,455,273 B2 * 10/2025 Sanden .................. G01N 33/24
(Continued)

FOREIGN PATENT DOCUMENTS

WO WO-2015189286 A1 * 12/2015 ............ G01J 3/0289
WO WO-2019167030 A1 * 9/2019 ............ E21B 49/00

*Primary Examiner* — Gordon J Stock, Jr.
(74) *Attorney, Agent, or Firm* — BelayIP

(57) ABSTRACT

Analysis of drill cores is performed by having an analysis system: process drill cores one drill core box at a time and obtain a three-dimensional point cloud representing the top surface of a drill core box being analyzed and any drill cores in the box with an optical scanner The control unit of the analysis system determines from the three-dimensional point cloud where there are drill cores in the drill core box and where is the location of the surface of a drill core at a plurality of locations and then directs the measurement head of the analysis system to perform a laser-induced breakdown spectroscopy measurement at at least a part of the plurality of locations. The control unit further adjusts the focus of the measurement head at each measurement location according to the determined position of the surface of the drill core at the location.

12 Claims, 2 Drawing Sheets

(51) Int. Cl.
*E21B 49/00* (2006.01)
*G01B 11/24* (2006.01)
*G01B 11/30* (2006.01)
*G01N 33/24* (2006.01)

(52) U.S. Cl.
CPC .............. *G01B 11/24* (2013.01); *G01B 11/30* (2013.01); *G01N 33/24* (2013.01)

(58) Field of Classification Search
CPC ..... G01B 11/303; G01B 11/306; G01B 11/24; G01B 11/002; G01B 11/005; G01B 11/14; G01B 11/16; G01B 11/22; G01N 33/24; G01N 21/718; G01N 21/3563; G01N 21/952
See application file for complete search history.

(56) References Cited

U.S. PATENT DOCUMENTS

| | | | | |
|---|---|---|---|---|
| 12,584,863 | B2 * | 3/2026 | Sanden ................ | G01N 21/718 |
| 2023/0314381 | A1 * | 10/2023 | Kangas ................... | B02C 19/18<br>73/12.01 |

* cited by examiner

METHOD AND SYSTEM FOR ANALYZING THE ELEMENTAL CONTENT OF DRILL CORES

CROSS REFERENCE TO RELATED APPLICATIONS

This application is a national phase application of International Application PCT/FI2023/000002, filed 28 Apr. 2023 which claims priority to Finnish priority patent application FI20227064 filed 30 Apr. 2022 and FI20227096 filed 6 Jul. 2022, the content of all of the aforementioned being incorporated herein by reference.

BACKGROUND OF THE INVENTION

Field of the Invention

This disclosure is directed to and otherwise concerns analysis of drill cores resulting from mining operations, ore exploration, well drilling and concrete sampling operations.

Description of Prior Art

Examination of drill cores is an old technique to gain information about rock composition in various depths below the surface of the earth. Drill cores are produced with hollow drills that leave a core intact, which can then be raised from the drill hole for analysis and storage. Drill core analysis is used in many different industries, such as in mining, in prospecting for minerals or oil, and in any situations where detailed information about composition of bedrock is desired.

Many different analysis methods are used in analyzing drill cores. Detailed information about the composition of a drill core can be obtained with X-ray fluorescence spectroscopy (XRF), which mainly provides information about elemental composition of a sample. Hyperspectral imaging can also be used to identify minerals in a sample.

Laser-induced breakdown spectroscopy (LIBS) is an analysis method in which surface of a sample is bombarded with a high peak power laser pulses which removes some material from the surface, heating the removed material to a plasma state. The spectra produced by the produced plasma is analyzed for identifying the elemental composition of the plasma, and consequently, of the surface at the point where the plasma was generated by the laser.

Analysis systems are typically complicated, expensive and require specialized personnel to operate, whereby analyses are typically performed in a central laboratory, to which drill cores are transported from the drilling site. Transport delays and possible analysis queues cause unwanted delays, whereby on-site analysis would often be desirable.

Small handheld devices exist for performing e.g. LIBS or XRF measurements. These are very useful for doing individual spot analyses onsite. However, handheld devices are quite cumbersome for thorough analysis of large numbers of cores.

A better system than known current systems is needed. An analysis system that could be deployed onsite would need to be simpler to use than typical current systems so that use of the system could be managed by personnel onsite at the drilling location. The system would also need to be able to cope with many different sizes and lengths of drill cores, even rubble, as drill cores may break even down to rubble depending on the consistency of the rock. Such a system would also need to be more economical to make it feasible to provide such a system onsite at a drilling location.

SUMMARY OF THE INVENTION

The invention disclosed in this disclosure solves the problems of prior art by having the analysis system process drill cores one drill core box at a time, obtaining a three-dimensional (3D) point cloud representing the top surface of a drill core box being analyzed and any drill cores in the box with an optical scanner, having the control unit of the analysis system determine from the 3D point cloud where there are drill cores in said drill core box, having the control unit determine the location of the surface of a drill core at a plurality of locations, having the control unit direct the measurement head of the analysis system to perform a laser-induced breakdown spectroscopy (LIBS) measurement at least a part of said plurality of locations, and having the control unit adjust the focus of the measurement head at each measurement location according to the determined position of the surface of the drill core at the location.

In an embodiment of the invention optical scanner is a laser profile scanner which is used to scan the whole drill core box.

In an embodiment of the invention, the focus of the measurement head is adjusted by moving the measurement head in the vertical dimension to bring the surface of the drill core to focus distance.

In a further embodiment of the invention, the focus of the measurement head is adjusted by moving an optical element within the measurement head to change the focus distance to match the distance to the surface of the drill core.

In a still further embodiment of the invention, the measurement head comprises autofocus detection functionality for detecting whether the focus point is on the surface of the sample, or whether the focus point is above or below the sample. Such functionality allows the analyzing system to correct small errors in focus at any measurement location. In a further embodiment of the invention, such autofocus mechanism is used for fine control of focus after coarse adjustment of focus based on the determination of surface location from said 3D point cloud.

A successful LIBS measurement requires a high power density of laser light on the surface of the sample, which practically requires that the laser light is well focused on the surface. In principle, it is possible to arrange an autofocus mechanism to manage the focus at all measurement locations. However, the inventors had the insight that determining the location of the drill core surfaces at various locations and using that information for adjusting focus at the same time as the measurement head is moved in the horizontal direction to the next measurement location allows higher scanning speeds, as there is no need to wait for the autofocus arrangement to reach and stabilize at the correct focus point at each measurement location. This advantage allows fast scanning speeds and fast coverage of large areas, e.g. over the whole top surfaces of a plurality of drill cores.

In an embodiment of the invention, the control unit is arranged to plan a route for the measurement head based on said 3D point cloud in order to optimize the movements of the measurement head while performing LIBS measurements along the route.

In a further embodiment of the invention, the control unit is arranged to determine the speed of movement of said measurement head at a plurality of locations along said route at least in part based on said 3D point cloud. In such an embodiment, the control unit can optimize the scanning speed of the measurement head for each location. For example, at a location where a drill core is broken into pieces and the top surfaces of the core pieces are uneven, the measurement head may need to be moved much more in the vertical direction compared to scanning an intact drill core, whereby an optimal scanning speed may be different for different locations.

As the measurement head is moved in a horizontal direction for performing LIBS measurements at different locations of a drill core surface or a surface of a broken piece of drill core, in an embodiment of the invention the measurement head needs to be moved in the vertical direction to bring the measurement head accurately to the correct focus distance from the sample surface at each location. While the top surface of an intact piece of drill core is rather flat and does not require a lot of vertical movement when the scanning is performed along the length of the drill core piece, the situation is different when performing measurements on uneven surfaces such as broken pieces of drill core or drill core rubble. When high measurement speeds are used, uneven surfaces of broken pieces of drill core require the vertical movements of the measurement head to be very fast in order to keep the measurement head within the correct focus distance.

In an embodiment of the invention, calculation of the movement of the measurement head is based at least in part on a mathematical model taking into account the physical parameters of the measurement head such as its mass as well as the physical parameters of the arrangement moving the measurement head such as the maximum movement speed and maximum acceleration that the arrangement moving the measurement head is able to provide. In such an embodiment, the vertical speed and vertical acceleration of the measurement head are calculated at a plurality of locations along a planned measurement route, and if the speed and/or acceleration exceeds the capabilities of the arrangement moving the measurement head, the planned horizontal speed of the measurement head is reduced at at least one location along the planned route in order to reduce the vertical movement speed and acceleration required by the planned route.

Such an embodiment of the invention allows maximizing the horizontal scanning speed on both intact pieces of drill cores as well as broken pieces of drill cores and rubble, while still allowing LIBS measurements to be performed on uneven spots on the sample surfaces as fast as the measurement system is able to track the uneven surface.

In high-resolution measurements the focus area size can be as small as 25 micrometers. Such a small focus area dimension requires that the focus distance from the measurement head to the sample surface needs to be controlled with similar precision. In an embodiment where the control of focus is managed by vertical movement of the measurement head, the vertical movements need to be very accurate and very fast, especially when high scanning and measurement speeds are required.

The inventors have found that moving the measurement head horizontally to a desired measurement location and thereafter adjusting the vertical position to match the focus distance to the sample surface results in slow individual measurements and long total scanning times. The inventors have found that adjusting the vertical position during horizontal movement so that the measurement head reaches the correct vertical position when reaching the desired horizontal position for a measurement provides a maximized measurement process speed.

In an embodiment of the invention moving the measurement head to the correct vertical position is started directly after the previous measurement, even before the measurement head has reached the correct horizontal position for the next measurement. Preferably, in such an embodiment, the horizontal movement speed between measurement locations is adjusted so that the measurement head is able to reach the correct vertical position before initiating the next measurement.

This way, the oncoming changes in the vertical position of the sample surface and consequently needed changes in the vertical position of the measurement head are anticipated by adjusting the horizontal movement speed by taking into account the limitations of vertical speed and acceleration that the measurement system is able to provide. For example, if a steep downward slope is approaching within a few next measurement locations, the horizontal speed of the measurement head is reduced early enough so that following of the surface height does not exceed the vertical speed and acceleration limitations, and that the measurement head is able to reach the needed vertical position when the measurement location is reached.

In an embodiment of the invention, the horizontal movement of the measurement head is not stopped for each LIBS measurement. Instead, the LIBS measurements are performed quickly enough that the horizontal movement during a single measurement is small enough not to meaningfully affect the measurement results. As a result, the scanning and measurement process is smooth and the movement of the measurement head does not need to be decelerated for the measurement and accelerated thereafter, which further increases the scanning speed of the system.

The recognition of where there are drill cores in the drill core box based on the 3D point cloud also reduces analyzing time, as that information can be used to skip scanning of sections of the drill core box which do not have a drill core present.

In an embodiment of the invention, the control unit is arranged to perform analysis of the spectra resulted from a LIBS measurement in order to determine elements present at the measurement location. In a further embodiment of the invention the control unit is arranged to determine which minerals are present in the sample, based on the relative concentrations of elements.

In a still further embodiment of the invention, the analysis system comprises a communication unit for data communication with external networks and servers. In such an embodiment, the analysis system can send the results to a remote server or a cloud service for more thorough analysis of the measurement results. Such an embodiment is beneficial, since analyzing of the presence of minerals or other compounds can be computationally heavy, and offloading heaviest calculations to remote services allows the analysis system to be light in computational resources and thus of lower cost than a system capable of heavy calculations.

The above summary relates to only one of the many embodiments of the invention disclosed herein and is not intended to limit the scope of the invention, which is set forth in the claims herein. These and other features of the present invention will be described in more detail below in the detailed description of the invention and in conjunction with the following figures.

BRIEF DESCRIPTION OF THE SEVERAL VIEWS OF THE DRAWINGS

Further advantages features and details of the various embodiments of this disclosure will become apparent from the ensuing description of a preferred exemplary embodiment and with the aid of the drawings. The features and combinations of features recited below in the description, as well as the features and feature combination shown after that in the drawing description or in the drawings alone, may be used not only in the particular combination recited, but also in other combinations on their own, with departing from the scope of the disclosure.

Various embodiments of the invention will be described in detail below, by way of example only, with reference to the accompanying drawings, of which.

DETAILED DESCRIPTION OF CERTAIN EMBODIMENTS

The following embodiments are exemplary. Although the specification may refer to "an", "one", or "some" embodiment(s), this does not necessarily mean that each such reference is to the same embodiment(s), or that the feature only applies to a single embodiment. Features of different embodiments may be combined to provide further embodiments.

In the following, features of the invention will be described with a simple example of a method and system for drill core analysis with which various embodiments of the invention may be implemented. Only elements relevant for illustrating the embodiments are described in detail. Details that are generally known to a person skilled in the art may not be specifically described herein.

Figure 1:
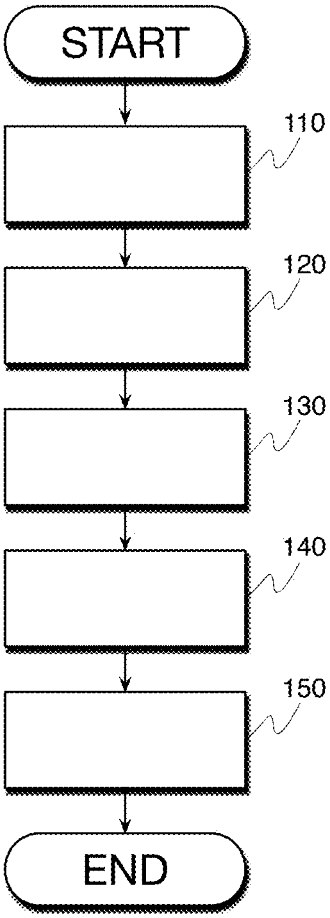
FIG. 1 illustrates a method according to an embodiment of the invention.

FIG. 1 illustrates a method according to an embodiment of the invention. The method is performed by a drill core analyzing system for analyzing the elemental content of drill cores. In this embodiment, drill cores are analyzed in batches of one drill core box at a time. In the example of FIG. 1, the method comprises the steps of

- forming 110 a 3D point cloud representing the surface of a drill core box and drill cores in said drill core box using an optical scanner,
- determining 120 from said 3D point cloud, where there are drill cores in the drill core box,
- determining 130 the position of the surface of a drill core at a plurality of locations on said drill core from said 3D point cloud,
- performing 140 a LIBS measurement at at least a part of said plurality of locations, and
- adjusting 150 the focus of the measurement head at each measurement location according to the determined position of the surface of the drill core at the location.

Figure 2:
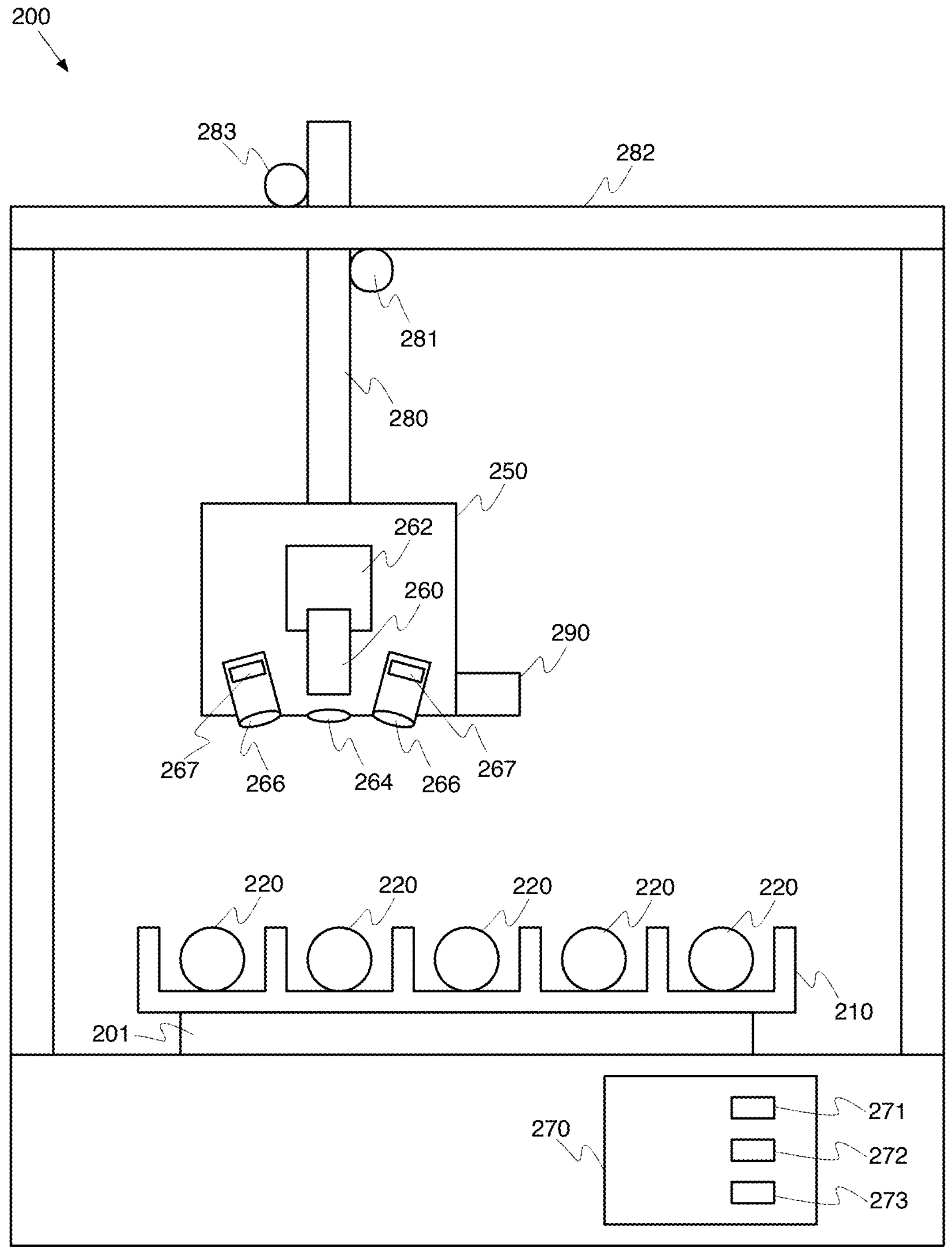
FIG. 2 illustrates a system according to an embodiment of the invention.

FIG. 2 illustrates a system 200 for analyzing the elemental content of drill cores according to an embodiment of the invention. FIG. 2 illustrates schematically several main components of the system.

The system has a measurement head 250 that comprises a laser unit 260, a laser cooling system 262, transmitting optics 264 for focusing the laser beam, as well as receiving optics 266 and a spectrometer sensor 267. The laser unit 260 can advantageously comprise a pulsed laser, as pulsed laser typically reaches high instantaneous power levels sufficient to ablate a part of the sample surface into plasma.

FIG. 2 also illustrates an exemplary embodiment in which the measurement head comprises one, two or more sets of receiving optics 266 and one, two or more spectrometer sensors 267. In this embodiment, these two sets are optimized for observing created plasma in different wavelength ranges: one of these sets is optimized for visible wavelengths while the other is optimized for ultraviolet wavelengths. Having more than one set of receiving optics and a spectrometer sensor allows covering of a wider wavelength range than with just one set. However, the invention is not limited to any specific number of these sets, as different embodiments of the invention may have one, two, three, or more sets of receiving optics and spectrometer sensors.

In a further embodiment of the invention the spectrometer sensor or sensors 267 are not situated in the measurement head, but the light gathered with receiving optics 266 is transferred to the spectrometer sensors 267 using one or more optical fiber cables. Such an embodiment allows the placement of the spectrometer sensors 267 in another location elsewhere in the system than within the measurement head, which reduces the mass of the measurement head. This is advantageous, since mass of the measurement head is one factor limiting the speeds in which the measurement head can be moved in different directions.

In an embodiment of the invention, the measurement head also comprises a nozzle connected to a blower unit for sucking air and dust from underneath the measurement head in order to remove dust produced by ablation of the sample surface by the laser.

The analyzing system 200 also comprises an arrangement for moving the measurement head 250 in three dimensions above the drill core box 210. The arrangement may comprise for example linear actuators or for example stepper motors moving the measurement head along linear guide rails. As an example, FIG. 2 shows a vertical rail 280 attached to the measurement head 250, which vertical rail 280 is moved in the vertical rail by a stepper motor 281. FIG. 2 also illustrates another stepper motor 283 moving the vertical rail 280 and consequently the measurement head 250 in a horizontal direction along a horizontal rail 282. A man skilled in the art knows many ways of arranging for moving an element in three dimensions under control of a control unit, wherefore these arrangements are not described in any further detail in this specification.

FIG. 2 also illustrates an optical profile scanner 290 attached to the measurement head 250. In an embodiment of the invention, before performing LIBS measurements, the system scans the drill core box and drill cores with the scanner 290 for obtaining a 3D point cloud representing the surface of the drill core box and any drill cores or pieces of drill cores within the box. The system then can use the 3D point cloud for controlling focus during LIBS measurements. In further embodiments of the invention, the system can use the 3D point cloud for determining a route for the measurement head to follow for performing the LIBS measurement, and for determining an optimal speed of movement of the measurement head along such a route. The optical profile scanner 290 can for example be a laser profile scanner or any other device that can provide a 3D point cloud representation of a surface, such as a LIDAR device or the optical profile scanner 290 can determine the 3D point cloud using stereophotogrammetry.

FIG. 2 also shows the control unit 270 for controlling the functioning of the analyzing system. In the embodiment illustrated in FIG. 2, the control unit comprises a processor 271, a memory element 272, and communication unit 273. The processor 271 can be any type of processor capable of executing instruction sets stored in a memory element.

The memory element 272 can in different embodiments of the invention be implemented in many ways known to a man skilled in the art. The memory element 272 can comprise transient memory elements such as random-access memory (RAM), and/or non-transient storage such as FLASH memory, magnetic disk based memory such as hard disks, or for example SSD disks.

The communication unit 273 can comprise for example circuitry for communicating via a wireless local area network (WLAN), or for example circuitry for communicating via a wireless cellular data transmission network. The communication unit 273 can in further embodiments of the invention also comprise circuitry for communicating via a wired connection such as an Ethernet connection. The communication unit allows connection to remote servers and cloud services which in various embodiments of the invention can be used for further processing of the measurement data such as for more detailed analysis and visualization of data, and for storing of measurement data.

The analyzing system 200 also comprises further electronics for aiding in the control of the system such as motor drivers and power sources. These can be implemented in the control unit, or as separate modules within the system. Various arrangements of these are well known to a man skilled in the art, whereby they are not described in further detail in this specification.

FIG. 2 also shows a drill core box 210 placed in the system for analysis. The drill core box 210 holds in the example of FIG. 2 a plurality of drill cores 220. In the example of FIG. 2, the system 200 also comprises rollers 201 that enable smooth and easy positioning of drill core box within the system.

In an embodiment of the invention the control unit comprises software which in addition for controlling the system provides functionality for data collection and storage, processing of data, analysis of measurement data and visualization of analysis results. In such an embodiment, the analysis system can provide measurement and analysis results locally, even if the system comprises no communication unit or if the site where the system is located does not have a data communication link to remote data networks.

In the following we describe an example of how a typical analysis procedure for analyzing a drill core box proceeds in the analysis system 200 shown in FIG. 2 according to an embodiment of the invention. The actions described here are performed by the control unit as directed by software executing on the processor of the control unit. The drill core box is scanned with the optical profile scanner to acquire a 3D point cloud representing a detailed surface map of the whole drill core box and any drill cores within it. Rock sample locations are determined from the point cloud data using measured intensity values and/or object recognition. An optimal movement route and movement speed of the measurement head is calculated from the point cloud data. Measurement locations are determined based at least partly on determined surface locations of the drill cores and scanning resolution selected by a user of the system. The LIBS measurements are executed along the predetermined areas by moving the measurement head over the samples along the determined route. The laser and spectrometers are triggered when the measurement head reaches a predefined measuring point.

In an embodiment of the invention, calculation of the movement route of the measurement head involves determination of coordinates of surface locations from the point cloud data, and determination of an optimal movement from a measurement location to the next measurement location, which minimizes time spent moving the measurement head to the next location. The measurement speed of the system is limited—among other factors—by the speed of movement in lateral and in vertical dimension. Since drill cores are long cylinders, one optimal solution is to maximise horizontal movement and minimize vertical movement by moving the measurement head from end to end of a drill core and performing measurements along that line of movement, before changing the vertical and crosswise positions and repeating the movement back to the other end of the drill core. Such a route would on average minimize movement of the measuring head between measurement locations.

The invention has many benefits. The invention provides a method and a system for analyzing drill cores, which can analyze a whole drill core box at a time, saving analyzing time. The invention also provides a system that can perform this analysis automatically, without requiring specialists to handle the system. Offloading more data processing and analysis to a remote server or a cloud service allows the processor of the system to be a relatively low power and economical processor, as high-end data processing capacity is not needed at the system. Providing the measurement results to a remote server or a cloud service also allows access for analysis experts in an event where review and analysis of an expert is needed. All these benefits make it feasible to provide an analysis system on-site at a mine or at an exploration project, whereby the system can provide quick insights to geologists and other users to support their decision making in operative mines or in ore exploration projects.

According to a first aspect of the invention, a method for analyzing the elemental content of drill cores is provided, the method being performed by a drill core analyzing system. In a first embodiment according to this first aspect of the invention, drill cores are analyzed in batches of one drill core box at a time, and the method comprises at least the steps of

- forming a 3D point cloud representing the surface of a drill core box and drill cores in said drill core box using an optical scanner,
- determining from said 3D point cloud, where there are intact drill cores or drill core pieces in the drill core box,
- determining the position of the surface of a drill core or a drill core piece at a plurality of locations from said 3D point cloud,
- planning the route of the measurement head of the drill core analyzing system at least in part based on said 3D point cloud,
- planning the speed of movement of said measurement head at a plurality of locations along said route at least in part based on said 3D point cloud in order to optimize the speed of movement of said measurement head,
- performing a laser induced breakdown spectroscopy measurement at a plurality of locations along said planned route, and
- adjusting the focus at each measurement location at least in part according to the determined position of the surface of the drill core or drill core piece at the location.

In a second embodiment of this first aspect of the invention, said step of planning the speed of movement of said measurement head comprises the steps of determining the vertical speed of said measurement head along said planned route required to maintain the measurement head at a predetermined focus distance from the surface of the drill core or drill core piece at measurement locations, and adjusting the planned horizontal speed of movement of said measurement head to keep said determined vertical speed under a predetermined limit.

In a third embodiment of this first aspect of the invention, said step of planning the speed of movement of said measurement head comprises the steps of determining the vertical acceleration of said measurement head along said planned route required to maintain the measurement head at a predetermined focus distance from the surface of the drill core or drill core piece at measurement locations, and adjusting the planned horizontal speed of movement of said measurement head to keep said determined vertical acceleration under a predetermined limit.

In a fourth embodiment of this first aspect of the invention, the method further comprises at least the step of analysing spectra resulted from a LIBS measurement to determine elements present at the measurement location.

In a fifth embodiment of this first aspect of the invention, the method further comprises at least the step of determining which minerals are present based on determined relative concentrations of elements.

In a sixth embodiment of this first aspect of the invention, the method further comprises at least the step of sending measurement results to a remote server for analysis.

According to a second aspect of the invention, a system for analyzing the elemental content of drill cores is provided. The system has a control unit for controlling the operations of the system. In a first embodiment according to this second aspect of the invention, the system comprises at least a measurement head for performing laser induced breakdown spectroscopy measurements under control of the control unit, an arrangement for moving said measurement head in three dimensions over a drill core box placed in said system for analysis, an optical scanner for measuring the location of the surface of a drill core box and of any drill cores in said drill core box, and the control unit is arranged to read measurement results from said optical scanner and for forming a 3D point cloud from said measurement results, to determine from a formed 3D point cloud where there are intact drill cores or drill core pieces in the drill core box, to determine the position of the surface of a drill core or a drill core piece at a plurality of locations from said 3D point cloud, to plan the route of the measurement head of the drill core analyzing system at least in part based on said 3D point cloud, to plan the speed of movement of said measurement head at a plurality of locations along said route at least in part based on said 3D point cloud in order to optimize the speed of movement of said measurement head, to direct said measurement head to perform a laser induced breakdown spectroscopy measurement at a plurality of locations, and to adjust the focus of the measurement head at each measurement location at least in part according to the determined position of the surface of the drill core or drill core piece at the location.

In a second embodiment according to this second aspect of the invention, the control unit is arranged to determine the vertical speed of said measurement head along said planned route required to maintain the measurement head at a predetermined focus distance from the surface of the drill core or drill core piece at measurement locations, and adjust the planned horizontal speed of movement of said measurement head to keep said determined vertical speed under a predetermined limit.

In a third embodiment according to this second aspect of the invention, the control unit is further arranged to determine the vertical acceleration of said measurement head along said planned route required to maintain the measurement head at a predetermined focus distance from the surface of the drill core or drill core piece at measurement locations, and adjust the planned horizontal speed of movement of said measurement head to keep said determined vertical acceleration under a predetermined limit.

In a fourth embodiment according to this second aspect of the invention, the control unit is further arranged to analyse spectra resulted from a LIBS measurement to determine elements present at the measurement location.

In a fifth embodiment according to this second aspect of the invention, the control unit is further arranged to determine which minerals are present based on determined relative concentrations of elements.

In a sixth embodiment according to this second aspect of the invention, the control unit is further arranged to send measurement results to a remote server for analysis.

In view of the foregoing description, it will be evident to a person skilled in the art that various modifications may be made within the scope of the invention. While a preferred embodiment of the invention has been described in detail, it should be apparent that many modifications and variations thereto are possible, all of which fall within the true spirit and scope of the invention.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the previous description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A method for analyzing the elemental content of drill cores, the method being performed by a drill core analyzing system, the method comprising the steps of:

automatically analyzing drill cores in batches of one drill core box at a time, forming a 3D point cloud representing a surface of a drill core box and drill cores in the drill core box using an optical scanner, determining from the 3D point cloud, where there are intact drill cores, drill core pieces or drill core pieces with an uneven top surface in the drill core box, determining a position of the surface of a drill core or a drill core piece at a plurality of locations from the 3D point cloud, planning a route of a measurement head of the drill core analyzing system at least in part based on the 3D point cloud, planning a speed of movement of the measurement head at a plurality of locations along the route at least in part based on the 3D point cloud in order to optimize a speed of movement of the measurement head, performing a laser induced breakdown spectroscopy measurement at a plurality of locations along a planned route, and adjusting a focus at each measurement location at least in part according to a determined position of the surface of the drill core or drill core piece at the location.

2. The method according to claim 1, wherein the step of planning the speed of movement of the measurement head further comprises the steps of:

determining a vertical speed of the measurement head along the planned route required to maintain the measurement head at a predetermined focus distance from the surface of the drill core or drill core piece at measurement locations, and adjusting a planned horizontal speed of movement of the measurement head to keep the determined vertical speed under a predetermined limit.

3. The method according to claim 1, wherein the step of planning the speed of movement of the measurement head further comprises the steps of, determining a vertical acceleration of the measurement head along the planned route required to maintain the measurement head at a predetermined focus distance from the surface of the drill core or drill core piece at measurement locations, and adjusting a planned horizontal speed of movement of the measurement head to keep the determined vertical acceleration under a predetermined limit.

4. The method according to claim 1, wherein the method further comprises at least the steps of analyzing spectra resulted from a LIBS measurement to determine elements present at the measurement location.

5. The method according to claim 4, wherein the method further comprises the step of determining which minerals are present based on a determined relative concentrations of elements.

6. The method according to claim 4, wherein the method further comprises the step of sending measurement results to a remote server for analysis.

7. A system for analyzing elemental content of drill cores, the system comprising a control unit configured to control operations of the system, wherein the system comprises:

a measurement head configured to perform laser induced breakdown spectroscopy measurements under control of the control unit, an arrangement configured to move the measurement head in three dimensions over a drill core box placed in the system, an optical scanner configured to measure a location of a surface of a drill core box and of any drill cores in the drill core box, and wherein the system is arranged and further configured to automatically analyze drill cores in batches of one drill core box at a time, and wherein the control unit is configured and arranged:

to read measurement results from the optical scanner and for forming a 3D point cloud from the measurement results, to determine from a formed 3D point cloud where there are intact drill cores, drill core pieces or drill core pieces with an uneven top surface in the drill core box, to determine a position of the surface of a drill core or a drill core piece at a plurality of locations from the 3D point cloud, to plan a route of the measurement head of the drill core analyzing system at least in part based on said 3D point cloud, to plan a speed of movement of the measurement head at a plurality of locations along the route at least in part based on the 3D point cloud in order to optimize a speed of movement of said measurement head, to direct said measurement head to perform a laser induced breakdown spectroscopy measurement at a plurality of locations, and to adjust a focus of the measurement head at each measurement location at least in part according to a determined position of the surface of the drill core or drill core piece at the location.

8. The system according to claim 7, wherein the control unit is further configured and arranged to:

determine a vertical acceleration of the measurement head along the planned route required to maintain the measurement head at a predetermined focus distance from the surface of the drill core or drill core piece at measurement locations, and adjust a planned horizontal speed of movement of the measurement head to keep the determined vertical acceleration under a predetermined limit.

9. The system according to claim 7, wherein the control unit is further configured and arranged to analyze spectra resulting from a LIBS measurement to determine elements present at the measurement location.

10. The system according to claim 7, wherein the control unit is further configured and arranged to determine which minerals are present based on determined relative concentrations of elements.

11. The system according to claim 7, wherein the control unit is further configured and arranged to:

determine a vertical speed of the measurement head along the planned route required to maintain the measurement head at a predetermined focus distance from the surface of the drill core or drill core piece at measurement locations, and adjust a planned horizontal speed of movement of the measurement head to keep the determined vertical speed under a predetermined limit.

12. The system according to claim 11, wherein the control unit is further configured and arranged to send measurement results to a remote server for analysis.

* * * * *